(12) United States Patent
Dees et al.

(10) Patent No.: US 6,493,570 B1
(45) Date of Patent: Dec. 10, 2002

(54) METHOD FOR IMPROVED IMAGING AND PHOTODYNAMIC THERAPY

(75) Inventors: H. Craig Dees; Timothy Scott, both of Knoxville, TN (US)

(73) Assignee: Photogen, Inc., Knoxville, TN (US)

( * ) Notice: Subject to any disclaimer, the term of this patent is extended or adjusted under 35 U.S.C. 154(b) by 0 days.

(21) Appl. No.: 09/184,388

(22) Filed: Nov. 2, 1998

(51) Int. Cl.$^7$ ................................................. A61B 5/00
(52) U.S. Cl. ..................... 600/411; 600/420; 600/427; 600/431; 607/88; 424/9.37; 424/9.4; 604/20
(58) Field of Search ..................... 600/407, 411, 600/427, 431, 420; 607/88, 89; 424/9.3, 9.362, 9.37, 9.4, 9.6, 9.61; 604/20

(56) References Cited

U.S. PATENT DOCUMENTS

| | | | |
|---|---|---|---|
| 4,599,227 A | 7/1986 | Dees et al. | 424/38 |
| 4,973,848 A | * 11/1990 | Kolobanov et al. | 250/458.1 |
| 5,128,139 A | 7/1992 | Brown et al. | 424/450 |
| 5,149,801 A | 9/1992 | Kahl et al. | 540/145 |
| 5,258,453 A | 11/1993 | Kopecek et al. | |
| 5,284,831 A | 2/1994 | Kahl et al. | 514/21 |
| 5,576,013 A | * 11/1996 | Williams et al. | 424/423 |
| 5,591,422 A | 1/1997 | Hemmi et al. | 424/362 |
| 5,654,423 A | 8/1997 | Kahl et al. | 540/145 |
| 5,827,186 A | * 10/1998 | Chen et al. | 600/407 |
| 5,829,448 A | 11/1998 | Fisher et al. | 128/898 |
| 5,832,931 A | 11/1998 | Wachter et al. | 128/898 |
| 5,998,597 A | 12/1999 | Fisher et al. | 536/23.1 |
| 6,042,603 A | 3/2000 | Fisher et al. | 607/89 |
| 6,331,286 B1 | 12/2001 | Dees et al. | |

FOREIGN PATENT DOCUMENTS

| | | |
|---|---|---|
| WO | WO 00/25819 | 5/2000 |
| WO | WO 00/25829 | 5/2000 |

OTHER PUBLICATIONS

Fisher, et al., "Clinical and Prelinical Photodynamic Therapy," *Lasers in Surgery and Medicine* 17:2–31 (1995).
Delpat et al., "A new liver function test: the elimination of rose bengal when injected into the circulation of human subjects", *Arch. Intern. Med.* 34, pp. 533–541 (1924).
Wilson, "Rose Bengal Staining of Epibulbar Squamous Neoplasms", *Opthalmic Surgery*, 7, pp. 21–23 (1976).
*Merck Index*, 12$^{th}$ Ed., entry 5055, 5068, 5069, 5071 (1996).
Young, S. et al, "Gadolinium(III) Texaphyrin: A Tumor Selective Radiation Sensitizer that is Detectable by MRI," *Proc. Natl. Acad. Sci.*, vol. 93, pp. 6610–6615, Jun., 1996.
Bernhard, E.J. et al, "Re–Evaluating Gadolinium (III) Texaphyrin as a Radiosensitizing Agent," *Cancer Research*, vol. 60, pp. 86–91, Jan. 1, 2000.

* cited by examiner

*Primary Examiner*—Ruth S. Smith
(74) *Attorney, Agent, or Firm*—Cook, Alex, McFarron, Manzo, Cummings & Mehler, Ltd.

(57) ABSTRACT

The present invention is directed to an apparatus and method of imaging and treatment using at least one photodynamic therapy ("PDT") agent. In particular, the apparatus and method is for imaging and treating diseased tissue.

22 Claims, 6 Drawing Sheets

METHOD FOR IMPROVED IMAGING AND PHOTODYNAMIC THERAPY

BACKGROUND OF THE INVENTION

The present invention is directed to an apparatus and method of imaging and treatment using at least one photodynamic therapy ("PDT") agent. In particular, the apparatus and method is for imaging and treating diseased tissue.

Imaging is typically performed to locate diseased tissue or tumors in a body. Once the diseased tissue is located, it is subsequently treated in some manner in order to destroy the diseased cells within this tissue. As explained infra, in the past, these were two separate procedures in a long, drawn out process that was frequently unsuccessful.

Imaging is generally performed using an imaging device such as CAT (Computerized Axial Tomography) scan or MRI (Magnetic Resonance Imaging). Alternatively, fluorography (using an image produced on a fluorescent screen by x-rays) or similar procedures can be used. Each of these imaging procedures requires a contrast agent for optimal performance. Examples of such imaging contrast agents include iodinated agents such as Omnipaque™ (Iohexol) and Omniscan™ (Gadodiamide) for x-ray based imaging or one of the various paramagnetic MRI contrast agents like gadolinium DPTA (Gd-DPTA).

Once the diseased tissue has been located via imaging, it needs to be treated. Such treatments, however, are often unsuccessful.

All current therapies for cancer (e.g., radiation and chemotherapy) function by attacking rapidly proliferating cells. Unfortunately, this targeting criterion does not limit the effects of treatment to cancer cells. As a consequence, such therapies are accompanied by undesirable side effects that may be life threatening. Furthermore, such therapies may actually reduce natural anti-tumor defenses. For example, radiation and chemotherapy damage the rapidly dividing cells of the immune system, suppressing anti-tumor and anti-infection responses.

Besides producing undesirable side effects, current therapies are largely incapable of achieving the desired potency of effects since they do not specifically attack cancer cells. Consequently, radiation or chemotherapy alone or in combination rarely cures cancer. Thus, the primary treatment for cancer is currently surgical removal of the tumor. This is commonly paired with adjuvant radiation and chemotherapy. Hence, to achieve a cure, the patient is surgically mutilated and poisoned by highly toxic treatments in an effort to destroy all cancer cells.

In an effort to minimize invasiveness of cancer treatment and improve overall efficacy, photodynamic therapy (PDT) has been developed. Photodynamic therapy is the combination of a photosensitive agent with site-specific illumination to produce a therapeutic response in certain tissues, such as a tumor. The agent attains an excited state when it absorbs a photon, and then is or becomes efficacious. Unfortunately, conventional single-photon excitation (SPE) methods used for the illumination step in PDT have not allowed PDT to reach its potential, primarily because (1) the high-energy light required for such treatment is incapable of penetrating deeply into tissue and (2) such illumination affords the physician with minimal spatial control of the treatment site. In contrast, the low-energy light used for two-photon excitation (TPE) PDT can safely penetrate tissue and provides three-dimensional control of treatment margins.

A more detailed explanation of TPE and SPE is provided in commonly owned U.S. Pat. No. 5,829,448, which is incorporated herein by reference.

While the use of two-photon excitation in PDT substantially ameliorates the depth of penetration and spatial control issues plaguing conventional PDT, additional improvements can be achieved by improvement of therapeutic performance of PDT agents and improvement of disease specificity in the selection of activation site. This is the consequence of several shortcomings of currently used agents and activation targeting approaches.

The only major PDT agent licensed by the Food and Drug Administration in the United States is the Type-II agent, porfimer sodium (or PHOTOFRIN™). This porphyrin-based agent is representative of a family of related agents (such as benzoporphyrin-derivative, $SnEt_2$, and Lutex) that are commonly activated via single-photon methods using light between 500 nm and 730 nm in wavelength. Such Type-II agents produce a therapeutic effect through the light-activated conversion (photocatalytic conversion) of oxygen into an unstable and toxic form (singlet oxygen) that destroys biological material. Unfortunately, this mechanism requires a rich supply of oxygen at the treatment site. This supply, however, can be quickly depleted, for example due to compromised blood supply (as is common in the center of a large tumor) or intense illumination (which can consume all available oxygen, preventing continued conversion into singlet oxygen). Thus, treatment of large tumors and the use of aggressive illumination methods are not practical with such agents. Further, agents like porfimer sodium must typically be administered systemically (via intravenous injection) at high dose levels well in advance of illumination (typically at least 24 hours in advance—increasing cost and inconvenience to the patient). Moreover, the high doses required for systemic administration are very expensive (up to $5,000 or more per dose) and cause persistent skin photosensitization.

The problems with porphyrin-based agents stem in part from the fact that these agents fail to achieve significant concentration in tumors. Rather, large doses administered systemically saturate all tissues. As a result, after a clearance time in the range of hours to days, single-photon excitation of residual agent at the treatment site produces not only the desired cytotoxic effect in the diseased tissue but can also damage healthy surrounding tissue by activation of the agent present there as well. It is this residual agent that also accounts for persistent skin photosensitization. Moreover, this family of agents is typified by relatively high toxicity without light activation (dark cytotoxicity). Light activation generally increases this toxicity only marginally (poor light-to-dark cytotoxicity ratio). While use of two-photon excitation can improve the performance of PDT with such agents, specifically by reducing or eliminating potential collateral damage during illumination, coupling TPE with an agent having improved biotargetting and light-to-dark cytotoxicity would dramatically enhance the safety and efficacy of PDT.

However, the ability to realize such advantages requires that the size, location and depth of the target be known precisely so that the light used for TPE can be precisely delivered to the target. Therefore, a new method that allows tumors or other diseased tissues to be identified and located quickly and precisely is required. Additional characteristics of such a method should solve other current problems with PDT, including: improved light-to-dark cytotoxicity ratio for the agent (and more specifically a very low dark cytotoxicity); improved accumulation of agent into diseased tissue with strong contrast between diseased and healthy tissue; and capability of combining imaging and therapy (such as through photoactivation of the agent in imaged locations). Further characteristics should include significantly reducing the cost of the agent and rapidly clearing the agent from normal tissue.

Therefore, it is an object of the present invention to meet these characteristics and to overcome the drawbacks in prior methods and agents.

SUMMARY OF THE INVENTION

The present invention is directed to a method and apparatus for imaging and treating diseased tissue using at least one PDT agent.

One embodiment of the method of the present invention includes the steps of administering a photo-active agent, the photo-active agent being retained in diseased tissue; and treating the diseased tissue with light sufficient to photo-activate the photo-active agent in the diseased tissue.

Preferably, the photo-active agent is a halogenated xanthene such as Rose Bengal.

A further embodiment of the method of the present invention includes the steps of administering a photo-active agent to a patient prior to or following imaging, the photo-active agent being retained in the diseased tissue; imaging the patient to identify the diseased tissue; and treating the imaged diseased tissue with light sufficient to photo-activate the photo-active agent in the imaged diseased tissue.

In a further embodiment, the photo-active agent is capable of acting as a contrast agent for CAT scanning, fluorography or related procedures.

In a further embodiment, the photo-active agent is capable of acting as a contrast agent for CAT scanning, fluorography or related procedures and being photo-activated in the diseased tissue.

In a further embodiment, the photo-active agent is capable of acting as a contrast agent for MRI and being photo-activated in diseased tissue.

In still a further embodiment, the photo-active agent is mixed with MRI, CAT scan, fluorography or related targeting or contrast agents prior to use.

In another embodiment of the present invention, the light source for performing PDT is integrated into or attached to an imaging device (e.g., CAT scan, MRI, or related devices). In a further embodiment, the method uses a light source in the combined PDT/imaging apparatus which causes two-photon excitation. In an alternative embodiment, the light source in the combined PDT/imaging apparatus causes single photon excitation.

DETAILED DESCRIPTION OF THE PRESENTLY PREFERRED EMBODIMENT

The present invention is directed to the apparatus and use of at least one PDT agent in imaging and treating diseased tissue.

The first embodiment of the present invention is directed to an improved method for photodynamic therapy which enhances performance through the use of a photo-active agent having superior light-to-dark cytotoxicity. This embodiment includes treating the diseased tissue with light so as to photo-activate the photo-active agent in the diseased tissue, thereby destroying the diseased tissue. Included in this embodiment is the step of administering a photo-active (PDT) agent to a patient. The PDT agent will preferably accumulate in the diseased tissue. Each of these steps, the PDT agent and further embodiments of the present invention based thereon, will be discussed in more detail infra.

Figure 1A:
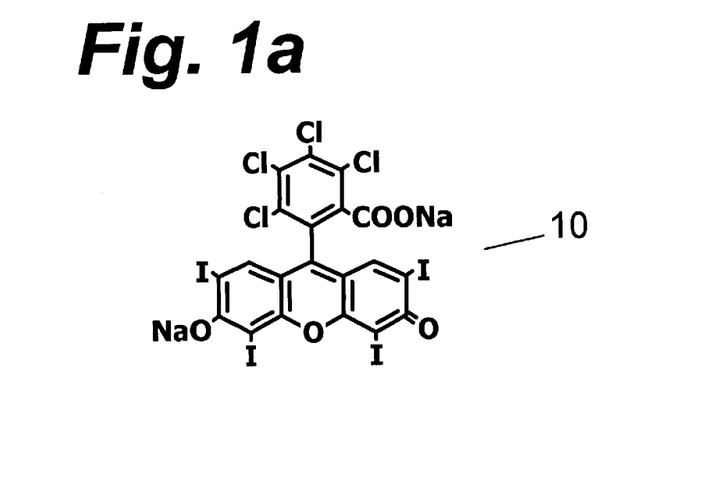
FIG. 1a is an illustration of the chemical structure of Rose Bengal.

One PDT agent which can be used in the present invention is Rose Bengal (4,5,6,7-tetrachloro-2',4',5',7'-tetraiodofluorescein); (see 10 in FIG. 1a). Rose Bengal is a Type-I PDT agent that is known to accumulate preferentially in (i.e. target) some tumors and other diseased tissues. Type-I agents produce a cytotoxic response through direct photochemical conversion into toxic substances, and their Type-I photodynamic action is thus oxygen independent. In the presence of oxygen, Rose Bengal is also capable of efficient singlet oxygen production (Type-II action), further enhancing its photodynamic potential. Indeed, the inventors of the present application have found that Rose Bengal is an extremely efficient PDT agent when compared to conventional PDT agents (such as porfimer sodium and other porphyrin-based agents that are limited to only Type-I or Type-II mechanism of action). For example, in vitro tests have shown that Rose Bengal at a concentration of ≦10 μg/mL is able to kill $10^7$ bacteria/mL within 5 seconds of illumination. Under similar conditions, porfimer sodium requires several hours to kill only a few percent of these bacteria. Therefore, in relation to porfimer sodium, Rose Bengal has an extremely high light-induced cytotoxicity. Moreover, Rose Bengal's dark cytotoxicity is negligible. Therefore, Rose Bengal has all the characteristics of a desirable replacement for porphyrin-based PDT agents: excellent biotargetting and high light-to-dark cytotoxicity ratio.

Figure 1B:
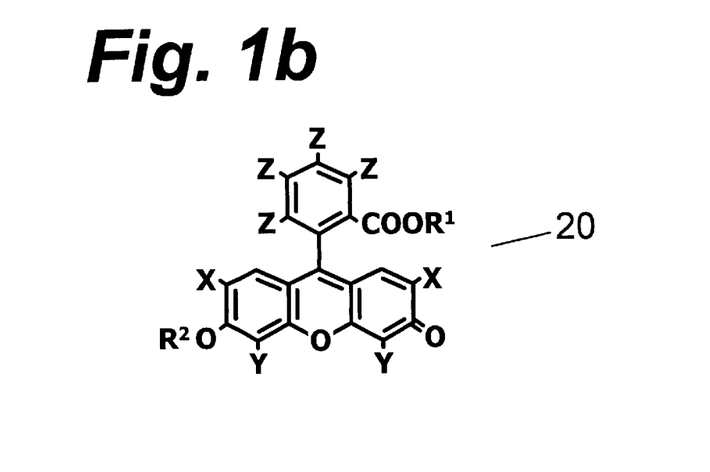
FIG. 1b is an illustration of the chemical structure of a halogenated xanthene.

Rose Bengal is a specific example of a class of photoactive agents that is preferably used in the present invention. These agents are referred to as halogenated xanthenes and are illustrated in FIG. 1b, where the symbols X, Y, and Z represent various elements present at the designated positions, and the symbols $R^1$ and $R^2$ represent various functionalities present at the designated positions. Physical and photochemical properties of representative halogenated xanthenes are summarized in Table 1. Porfimer sodium, the most common PDT agent presently in use, is also listed for comparison of related properties.

TABLE 1

Physical and Photochemical Properties of Example Halogenated Xanthenes:

| Compound | Substitution | | | | | MW (g) | $\lambda_{max}$ (nm) | | |
|---|---|---|---|---|---|---|---|---|---|
| | X | Y | Z | $R^1$ | $R^2$ | | $H_2O$ | EtOH | MeOH |
| Fluorescein | H | H | H | Na | Na | 376 | 490 | 499 | 492 |
| | Cl | H | H | Na | Na | 445 | 502 | 511 | |
| | H | Cl | H | Na | Na | 445 | 502 | 511 | |
| | H | H | Cl | H | H | 470 | 515 | | |
| | Cl | Cl | H | Na | Na | 514 | 510 | 520 | |
| Dibromofluorescein | Br | H | H | Na | Na | 534 | 504 | 510 | |
| Solvent Red 72 | H | Br | H | H | H | 490 | | | 450 |
| Diiodofluorescein | I | H | H | Na | Na | 628 | 506 | 513 | |
| Eosin B | $NO_2$ | Br | H | Na | Na | 624 | 522 | | |
| Eosin Y | Br | Br | H | Na | Na | 692 | 517 | 523 | 527 |
| Ethyl Eosin | Br | Br | H | $C_2H_5$ | K | 714 | | 532 | |
| Erythrosin B | I | I | H | Na | Na | 880 | 528 | 532 | 529 |
| Phloxine B | Br | Br | Cl | Na | Na | 830 | 541 | 548 | 547 |
| Rose Bengal | I | I | Cl | Na | Na | 1018 | 547 | 557 | 556 |
| | I | I | Cl | Li | Li | 986 | | 559 | |
| | I | I | Cl | $C_2H_5$ | $(C_2H_4)_3NH$ | 1100 | | 563 | |
| | I | I | Cl | $(C_2H_5)_3NH$ | $(C_2H_4)_3NH$ | 1166 | | 559 | |
| Porfimer Sodium | | | | | | 1200 | 368 | | |

| Compound | $\alpha$ ($cm^{-1} \cdot mol^1 \cdot L$) | $\lambda_{em}$ (nm) | | | $\phi$ (fluor) | $\phi$ (triplet) | $\phi$ (singlet oxygen) | | |
|---|---|---|---|---|---|---|---|---|---|
| | | $H_2O$ | EtOH | MeOH | MeOH | MeOH | $H_2O$ | EtOH | MeOH |
| Fluorescein | $6.4 \times 10^4$ | 519 | 519 | 518 | 0.93 | 0.03 | 0.03 | 0.03 | 0.09 |
| | | | | | | | 0.04 | 0.07 | |
| | | | | | | | 0.04 | 0.07 | |
| | $2.9 \times 10^4$ | | | | | | | | |
| | | | | | | | 0.05 | 0.05 | |
| Dibromofluorescein | $1.4 \times 10^4$ | | | | | | 0.32 | 0.42 | |
| Solvent Red 72 | $1.4 \times 10^4$ | | | | | | | | |
| Diiodofluorescein | $5.8 \times 10^4$ | | | | 0.03 | | 0.33 | 0.48 | |
| Eosin B | $3.9 \times 10^4$ | | | | 0.00 | | | | |
| Eosin Y | $9.1 \times 10^4$ | 538 | 544 | 541 | 0.63 | 0.28 | 0.32 | 0.57 | 0.39 |
| Ethyl Eosin | $1.1 \times 10^4$ | | 560 | | 0.70 | | | | |
| Erythrosin B | $9.1 \times 10^4$ | 547 | 553 | 551 | 0.08 | 0.62 | 0.69 | 0.63 | 0.62 |
| Phloxine B | $1.0 \times 10^5$ | 556 | 565 | 563 | 0.30 | | 0.40 | 0.63 | |
| Rose Bengal | $1.0 \times 10^5$ | 568 | 566 | 573 | 0.08 | 0.76 | 0.86 | 0.75 | 0.76 |
| | | | 572 | 568 | | | | | |
| | | | 590 | 585 | | | | | 0.74 |
| | | | 569 | 573 | | | | | 0.72 |
| Porfimer Sodium | $2.0 \times 10^5$ | | | | | | >0.7 | | |

In general, halogenated xanthenes are characterized by a low dark cytotoxicity, a high light cytotoxicity, a high single-photon cross-section extending from approximately 300 nm to 600 nm, and photochemical properties that are substantially unaffected by the local chemical environment or the attachment of functional derivatives at positions $R^1$ and $R^2$. Moreover, the halogenated xanthenes will target some tumors or other diseased tissues based on selective partitioning properties.

The facility with which the halogenated xanthenes target specific tissues or other sites can be further optimized by attachment of specific functional derivatives at positions $R^1$ and $R^2$, so as to change the chemical partitioning or biological activity of the agent. For example, attachment of one targeting moiety or more at positions $R^1$ or $R^2$ can improve targeting to specific tissues, such as cancerous tumor tissues or sites of localized infection. These targeting moieties include DNA, RNA, amino acids, proteins, antibodies, ligands, haptens, carbohydrate receptors or complexing agents, lipid receptors or complexing agents, protein receptors or complexing agents, chelators, and encapsulating vehicles.

Thus, one example of this feature would be to combine Rose Bengal with a lipid (at position $R^1$. via esterification), so as to increase the lipophilicity of Rose Bengal, and thereby modify its targeting properties in the patient. Such a modified agent could be administered directly as a micelle suspension, or delivered in conjunction with a delivery vehicle, such as a surfactant, and would exhibit increased targeting to tumor cells. Suitable formulations of such an agent include topical creams and lotions, and liquids for intravenous, parenteral or intratumoral injection.

Figure 2:
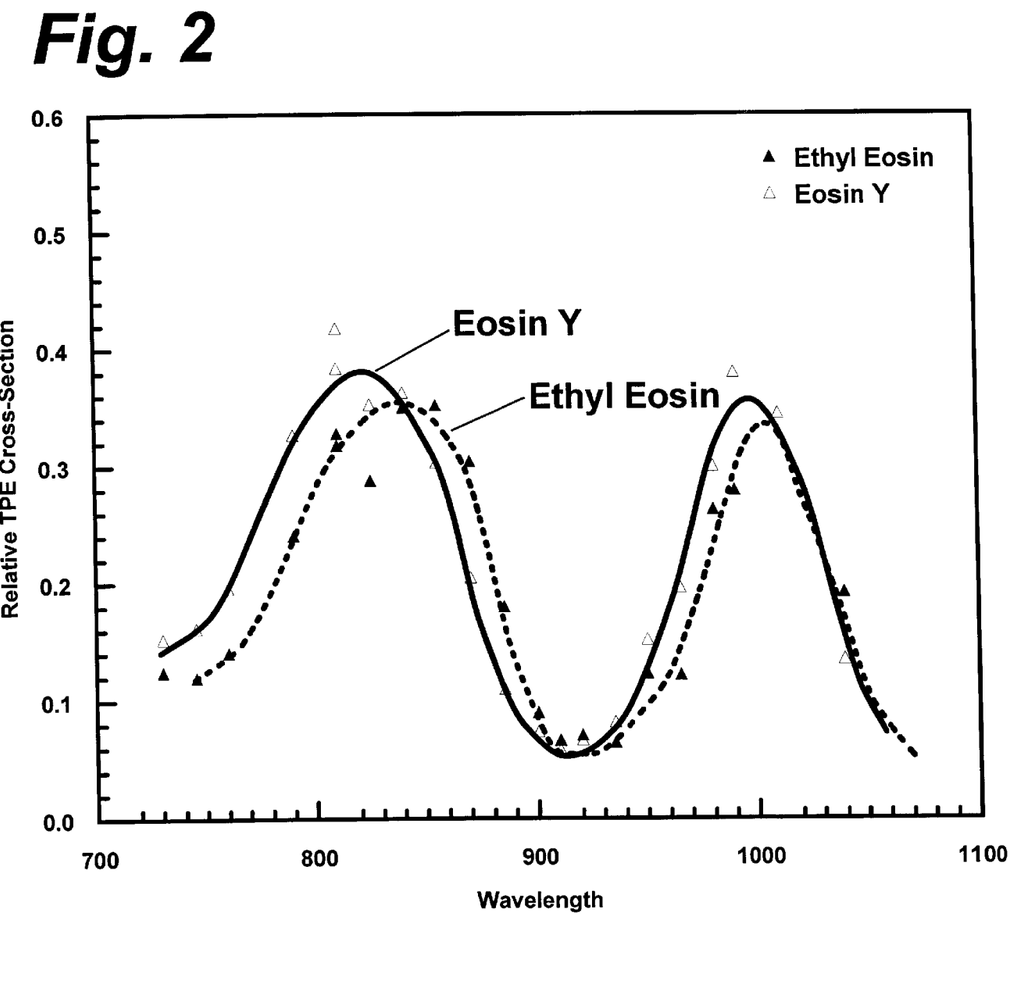
FIG. 2 is an illustration of the two photon cross-section for several example halogenated xanthenes.

In addition to having desirable SPE characteristics, the halogenated xanthenes afford attractive properties for TPE. Specifically this class of agent offers broad and intense TPE spectral response across a range wavelengths extending from greater than 730 nm to less than 1100 nm, as shown in FIG. 2. More specifically, attachment of moieties at positions $R^1$ and $R^2$ elicit insignificant changes in TPE spectral properties, as is clear, for example, by comparison of the spectral response of Eosin Y (wherein $R^1$=Na) and Ethyl Eosin (wherein $R^1$=$OCH_2CH_3$ ). Thus, attachment of targeting agents is possible without significantly affecting the photochemical properties of the agent.

Therefore, the halogenated xanthenes constitute excellent PDT agents for both SPE and TPE activation mechanisms, and can be used directly or in derivatized form to improve, for example, solubility or biotargetting through attachment of various functionalities at positions $R^1$ and $R^2$. Accordingly, in a preferred embodiment of the present invention, at least one halogenated xanthene or halogenated xanthene derivative is used as a PDT agent. The PDT agent can be given orally, systemically (e.g. by an injection), or topically, in a manner well known in the art. It is further preferred that Rose Bengal be used as the PDT agent. Such agent can be activated using single-photon excitation, or preferably two-photon excitation.

In a further embodiment of the present invention, the selectivity of photodynamic activation is improved though use of conventional imaging methods to identify diseased tissue targets. For example, x-ray based imaging, such as Computerized Axial Tomography (CAT scan), fluorography or other related procedures, or Magnetic Resonance Imaging (MRI) is used to detect the location of diseased tissue. Such imaging works by detecting abnormalities in the distribution or properties of tissue components (such as density), the presence or absence of certain materials, or the uptake or exclusion of imaging contrast agents. Such diseased tissue is then used as the target for selective optical activation of photodynamic agent administered to the patient, thereby selectively destroying such diseased tissue.

The inventors of the present invention have discovered that certain PDT agents, and more specifically the halogenated xanthenes, are not substantially photodynamically activated nor destroyed by exposure to the energies commonly used for x-ray or MRI imaging. Accordingly, these agents are safe to administer prior to such diagnostic procedures. Hence, the PDT agent may be administered to the patient prior to diagnosis (thereby potentially reducing delay between diagnosis and treatment) or following diagnosis (thereby reducing unnecessary administration of agent in cases where no disease is detected).

Therefore, a preferred embodiment of the present invention comprises the steps of x-ray or MRI imaging via conventional means to detect the presence of diseased tissue; administering a PDT agent, preferably a halogenated xanthene, prior to or upon detection of such diseased tissue, and directing light, appropriate for SPE or preferably TPE activation methods, as discussed infra, upon or to such detected diseased tissue sufficient to activate the PDT agent and thereby selectively destroy substantially only such diseased tissue.

In a further embodiment of the present invention, the efficacy of the detection or imaging step in the preceding embodiment is further improved through the use of an imaging contrast agent. In particular, the PDT agent, and more specifically, a halogenated xanthene, is mixed with an imaging contrast agent, such as for example, x-ray contrast agents like Omnipaque™ (Iohexol) and Omniscan™ (Gadodiamide) or one of the various paramagnetic MRI contrast agents like gadolinium DPTA (Gd-DPTA). For example, Rose Bengal is compatible in solution with agents such as Omnipaque™, Omniscan™, and Gd-DPTA, and exhibits similar biotargetting properties. The mixture is then administered to the patient. Following administration of such a mixture of contrast agent and PDT agent, conventional imaging (such as, for example CAT scan or MRI) is used to locate diseased tissue based on response of the conventional contrast agent, then the PDT agent, co-located in the diseased tissue, would be activated at the site of the detected diseased tissue using SPE or more preferably TPE to destroy such diseased tissue.

The inventors have shown that Rose Bengal is capable of selective photodynamic activation in a liver model, following administration of the agent in solution. Such a model is also known to accumulate conventional x-ray and MRI contrast agents. Thus, the inventors have shown that it is feasible to deliver conventional imaging contrast agents and PDT agents to target tissues, and that such agents will retain their respective activities in the target tissues, allowing combined detection and treatment of diseased tissue at locations indicated by imaging based on detected imaging contrast agents. Hence, one preferred embodiment of the present invention is to jointly administer, either sequentially (for example via injections or intravenous drip) or more preferably as a single, mixed solution, one or more x-ray or MRI contrast agent with one or more PDT agent, preferably an halogenated xanthene agent, and subsequently to direct activation of the one or more PDT agent based on imaging data obtained utilizing the one or more contrast agent.

In another embodiment of the present invention, the PDT agent also acts as a contrast agent for imaging. The use of the same agent for both imaging and treatment procedures is highly advantageous. For example, it eliminates the need for a second dose of an agent. Such a second dose requires further time between imaging and treatment, as the second agent, after being administered, must accumulate in the diseased tissue before treatment can begin. Further, use of a second agent makes the process more costly and requires the patient to be subjected to a second application of a foreign substance.

Figure 3:
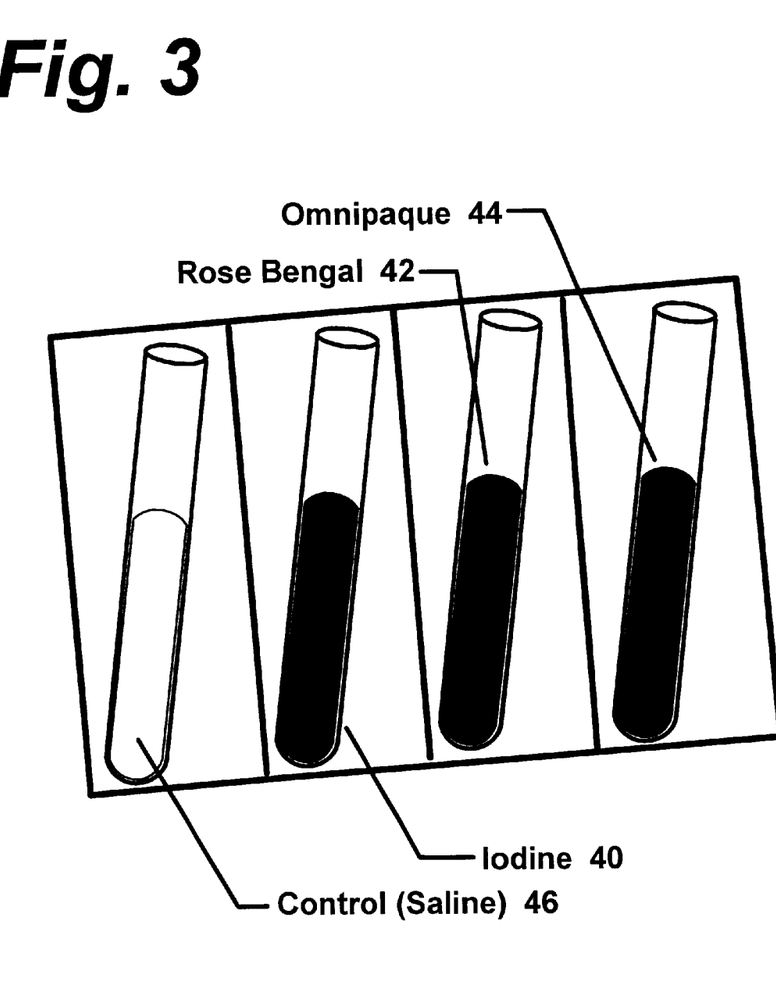
FIG. 3 illustrates the CAT scan image of test tubes of Rose Bengal, x-ray contrast agents and a control.
Figure 4:
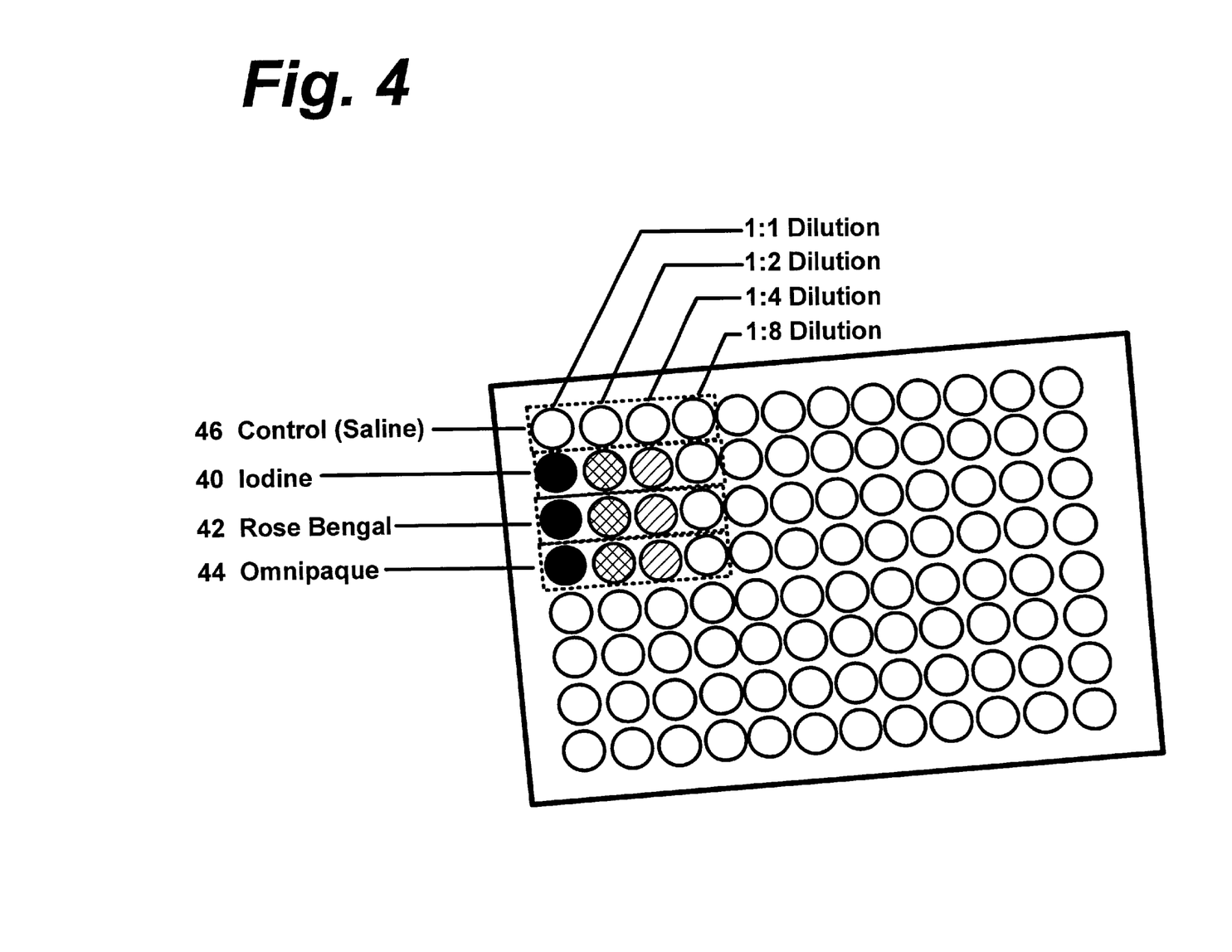
FIG. 4 illustrates a CAT scan of a range of concentrations of the solutions of FIG. 3.

More specifically, the chemical structure of the halogenated xanthenes, which have a high electron density due to their significant halogen content, renders them opaque to x-rays. For example, Rose Bengal is highly opaque to the x-rays used for CAT scan or normal x-ray imaging. FIGS. 3 and 4 illustrate the opaqueness of Rose Bengal versus standard x-ray contrast agents and a control. These figures are drawings of actual pictures of experiments done by the inventors of the present invention. For example, the CAT scan image of test tubes containing various solutions shown in FIG. 3 demonstrates that iodine 40 (350 mgI/mL in aqueous base), Rose Bengal 42 (225 mg halogen/mL in saline), and Omnipaque™ 44 (350 mgI/mL Iohexol) have similar x-ray densities. Furthermore, these densities are dramatically greater than that of a control 46 (saline). A CAT scan image of various dilutions of these same solutions (held in wells in a 96-well sample plate) illustrated in the drawing in FIG. 4 further demonstrates that Rose Bengal 42 shows comparable response to that of the standard x-ray contrast agents 40, 44 across a range of concentrations.

Figure 5:
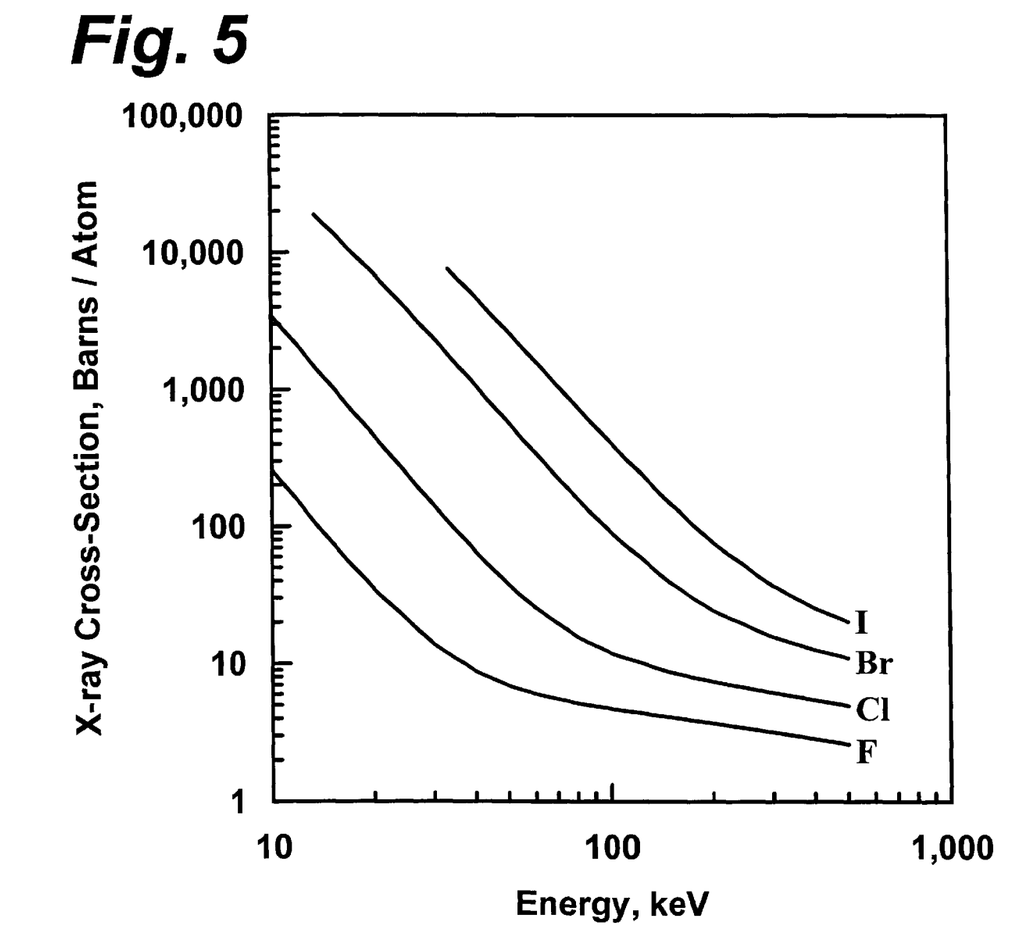
FIG. 5 is a graph of energy versus x-ray cross-section for halogens.

FIG. 5 demonstrates that strong absorption for the halogens occurs well below the energies used for standard diagnostic x-ray devices, which generally use energies greater than 50 keV. Therefore, the halogen content of the halogenated xanthenes makes this class of photodynamic agent potent x-ray contrast agents. Since x-ray cross-section increases substantially in the order F<Cl<Br<I, it is preferred that those halogenated xanthenes with a large content of I or Br be used for x-ray contrast. For example, Table 1 indicates that Rose Bengal, Phloxine B. Erythrosin B, and Eosin Y will have larger x-ray cross-sections than Solvent Red or Eosin B as a consequence of respective differences in halogen content, and will thereby be preferred for use as x-ray contrast agents. More preferably, the high iodine content of Rose Bengal makes this agent the most attractive x-ray contrast agent of this class.

Thus, certain special PDT agents, preferably the halogenated xanthenes, can be used as contrast agents for x-ray based detection and imaging of tissue for the detection of disease. This is based on the tissue specificity of such agents and their large x-ray density. Hence, it is a further preferred embodiment to use such agents as x-ray contrast agents.

Such agents will in general retain their photodynamic ability under such conditions of use and can thereby be used for x-ray based detection of diseased tissue followed by image-guided photodynamic activation, using SPE or preferably TPE activation methods, so as to selectively destroy such diseased tissue. Since both x-ray density and photodynamic efficiency are greatest for those halogenated xanthenes with a large content of I or Br, such agents will be optimal and preferred for combined x-ray imaging and subsequent site-specific PDT activation based on results of such imaging. Table 1 shows that Rose Bengal, Phloxine B. Erythrosin B, and Eosin Y, for example, have high efficiency in singlet oxygen generation, and are also extremely efficient PDT agents. Thus, it is a further preferred embodiment of the present invention to use halogenated xanthenes, and more preferably the iodinated or brominated halogenated xanthenes, as combined x-ray contrast and PDT agents, wherein x-ray imaging is used to direct subsequent activation of such agent using SPE or preferably TPE activation methods.

In addition to the aforementioned use of the halogenated xanthenes as x-ray contrast agents, the unique structural features of these agents make such agents attractive candidates as MRI contrast agents. Although not paramagnetic like the majority of conventional MRI contrast agents, the halogenated xanthenes contain aromatic protons which exhibit characteristic MRI signatures based on the chemical shift of such protons. Further, the presence of substantial densities of aromatic halides in the halogenated xanthenes constitutes a further unique and useful MRI signature based on detection of resonances from such aromatic halides. Since proton and halogen nuclear magnetic resonance are relatively sensitive phenomena (for example, F, Br and I have many-fold higher sensitivities relative to carbon-13 NMR, as shown in Table 2), MRI detection and imaging based on the presence of the halogenated xanthenes in diseased tissue represents a further unique and attractive medical application for such agents. Hence, it is a further preferred embodiment of the present invention to utilize the halogenated xanthenes as MRI contrast agents, and to use imaging data based on detection of such agents to selectively direct the subsequent photoactivation of such agents present in diseased tissue using SPE and preferably TPE activation methods. Since the majority of installed MRI devices are based on detection of proton resonance, it is further preferred that such MRI detection be performed based on resonance of aromatic protons present in the halogenated xanthenes.

photo-activate the agent associated with the diseased tissue. Preferably, laser light is used. Alternate light sources include light emitting diodes, micro-lasers, monochromatic or continuum lasers or lamps for production of activating light, and continuous wave or pulsed lasers or lamps. Either single-photon or two-photon excitation methods can be used for agent activation. A more detailed explanation of such excitation methods is given in commonly assigned U.S. Pat. No. 5,829,448 which is incorporated herein by reference. The excitation of the photo-active agent starts a process which eventually kills the cells in the diseased tissue.

Figure 6:
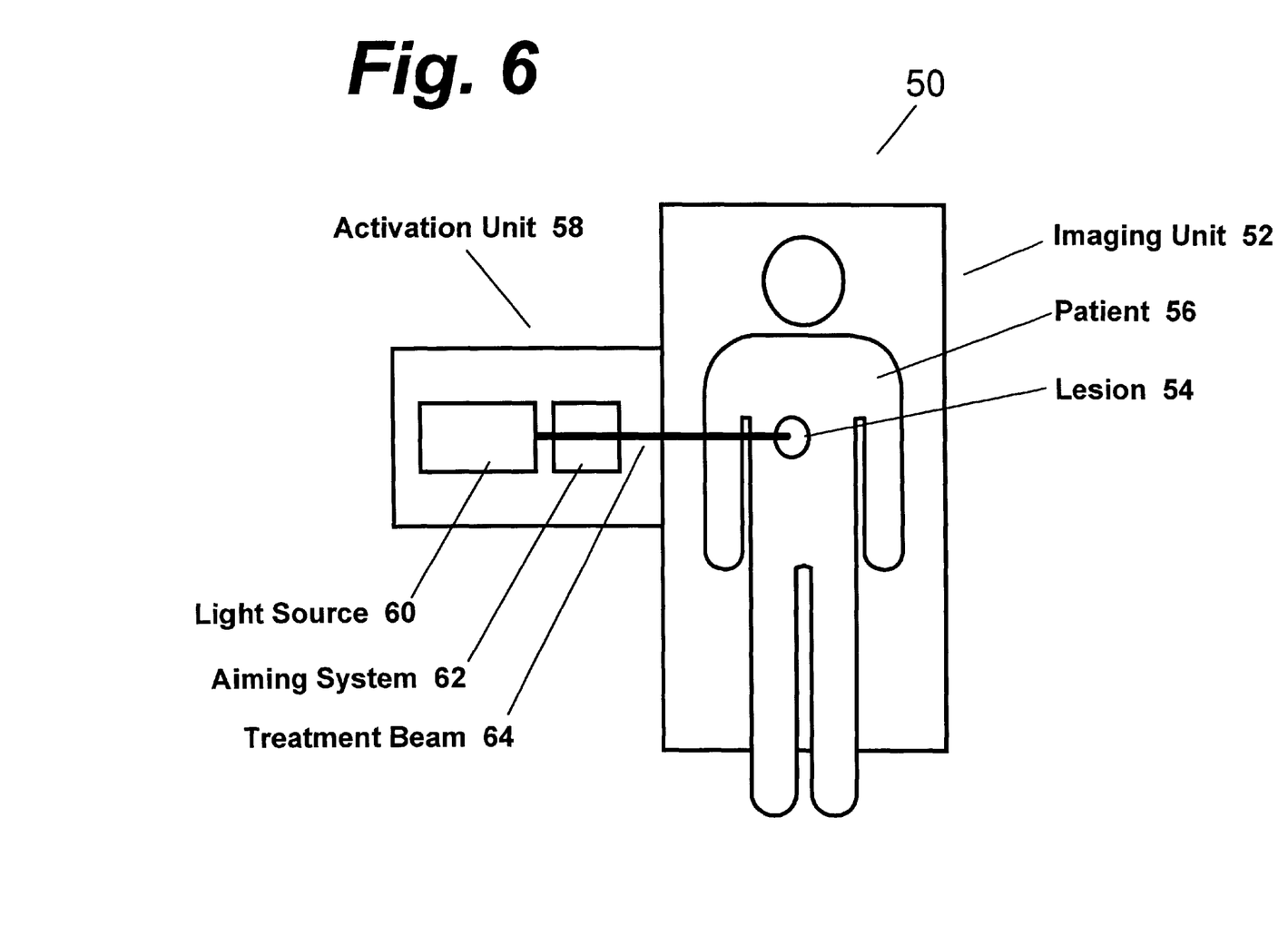
FIG. 6 illustrates a combined imaging and treatment device in accordance with the present invention.

In a further embodiment of the present invention, the light source used for photodynamic activation is integrated into or onto the imaging device, such as an MRI system or x-ray imaging device. An example of such a device for imaging and treatment 50 is illustrated in FIG. 6. Such a combined imaging and treatment device allows more precise delivery of treatment to diseased tissue based on improved accuracy of registration between imagery data and treatment targets. FIG. 6. for example, shows a conventional imaging unit 52, such as a CAT scan or MRI system, used to identify a lesion 54 present in a patient 56. Imaging of this lesion can be done by one of the methods discussed supra or by other known methods of imaging. This lesion 54 then serves as the target for an integrated activation unit 58 that serves selectively to photoactivate PDT agent present in the lesion. The activation unit 58 preferably includes a light source 60, such as, for example, a laser capable of SPE activation of the agent and more preferably a laser capable of TPE activation of such agent, such as a mode-locked titanium:sapphire or neodymium YLF laser. Preferably, the activation unit 58 also includes an aiming system 62, such as, for example, a mirror-based galvanometer or other optical scanning system. Constructed and functioning in this manner, the imaging unit 52 can be made to guide application of light 64 produced by the activation unit 58, for example under manual control of a physician or more preferably under automated or semi-automated computer control, such that the activating light 64 is applied substantially only to the site of the detected lesion 54, thereby improving safety and efficacy of the treatment process.

A mode-locked titanium:sapphire laser is a preferred embodiment for the light source for the integrated activation unit. Such a laser is capable of producing a rapid series of high peak power pulses of NIR light that are well suited for TPE of the halogenated xanthenes. Standard, commercially available mode-locked titanium:sapphire lasers are capable of outputting mode-locked pulses with durations <200 fs with pulse energies of about 1–20 nJ at pulse repetition frequencies in excess of 75 MHz. This constitutes a quasi-

TABLE 2

Magnetic Resonance Properties of Elements:

|  | $^{1}H$ | $^{13}C$ | $^{19}F$ | $^{35}Cl$ | $^{37}Cl$ | $^{79}Br$ | $^{81}Br$ | $^{127}I$ |
|---|---|---|---|---|---|---|---|---|
| Atomic Number | 1 | 6 | 9 | 17 | 17 | 35 | 35 | 53 |
| Atomic Mass ($^{12}C$ = 12.0000) | 1.00 | 13.00 | 19.00 | 34.97 | 36.97 | 78.92 | 80.92 | 126.90 |
| Natural Abundance (%) | 99.98 | 1.02 | 100.00 | 75.53 | 24.47 | 50.54 | 49.46 | 100.00 |
| Spin Quantum Number | 1/2 | 1/2 | 1/2 | 3/2 | 3/2 | 3/2 | 3/2 | 5/2 |
| NRM Frequency (MHz at 1 Tesla) | 42.58 | 10.70 | 40.06 | 4.17 | 3.47 | 10.67 | 11.50 | 8.52 |
| NMR Sensitivity at Constant Field (relative to $^{1}H$) | 1.00 | $1.6 \times 10^{-2}$ | 0.83 | $4.7 \times 10^{-3}$ | $2.7 \times 10^{-3}$ | $7.9 \times 10^{-2}$ | $9.8 \times 10^{-2}$ | $9.3 \times 10^{-2}$ |
| NMR Sensitivity at Constant Frequency (relative to $^{1}H$) | 1.00 | 0.25 | 0.94 | 0.49 | 0.41 | 1.25 | 1.35 | 2.33 |

Following imaging in the present invention, light is applied via a light source to the disease site in order to continuous beam of light having a relatively low average power (up to several Watts) but high peak power (on the order of 100 kW) that is continuously tunable over a NIR wavelength band from approximately 690–1080 nm. The pulse train from such a source is easily aimed using standard optical means, such as reflective or refractive optics, so as to be directed onto or into a lesion or other localized treatment target. Other light sources suitable for activation of photodynamic agents include: continuous wave and pulsed lamps, diode light sources, semiconductor lasers; other types of gas, dye, and solid-state continuous, pulsed or mode-locked lasers, including: argon ion lasers; krypton ion lasers; helium-neon lasers; helium-cadmium lasers; ruby lasers; Nd:YAG, Nd:YLF, Nd:YAP, Nd:YVO4, Nd:Glass, and Nd:CrGsGG lasers; Cr:LiSF lasers; Er:YAG lasers; F-center lasers; Ho:YAF and Ho:YLF lasers; copper vapor lasers; nitrogen lasers; optical parametric oscillators, amplifiers and generators; regeneratively amplified lasers; chirped-pulse amplified lasers; and sunlight.

This description has been offered for illustrative purposes only and is not intended to limit the invention of this application, which is defined in the claims below.

What is claimed as new and desired to be protected by letters patent is set forth in the appended claims.

We claim:

1. A method of imaging diseased tissue comprising the steps of:
   administering a halogenated xanthene to a patient prior to imaging, a portion of said halogenated xanthene being retained in said diseased tissue; and
   imaging said patient using a detected signal from said halogenated xanthene to contrast and identify said diseased tissue.

2. The method of claim 1 wherein said halogenated xanthene is Rose Bengal.

3. The method of claim 1 wherein said halogenated xanthene includes as a functional derivative a targeting moiety selected from the group consisting of deoxyribonucleic acid (DNA), ribonucleic acid (RNA), amino acids, proteins, antibodies, ligands, haptens, carbohydrate receptors or complexing agents, lipid receptors or complexing agents, protein receptors or complexing agents, chelators, and encapsulating vehicles.

4. The method of claim 1 wherein said imaging is accomplished through a method selected from the group consisting of computerized axial tomography, fluorography and magnetic resonance imaging.

5. The method of claim 1 wherein said halogenated xanthene is selected from the group consisting of iodinated and brominated halogenated xanthenes.

6. The method of claim 1 wherein said halogenated xanthene is selected from the group consisting of Rose Bengal, Phloxine B, Erythrosin B and Eosin Y.

7. The method of claim 1 wherein said halogenated xanthene is detected based on resonance of aromatic protons in said halogenated xanthene.

8. The method of claim 1 wherein said halogenated xanthene is detected based on resonance of aromatic halides in said halogenated xanthene.

9. A method of locating and treating diseased tissue comprising the steps of:
   administering to a patient an imaging contrast agent which comprises a halogenated xanthene;
   imaging diseased tissue in the patient by using said contrast agent to promote image contrast and identify said diseased tissue; and thereafter
   targeting and photo-activating the halogenated xanthene as a photodynamic therapy (PDT) agent at locations determined in said imaging step.

10. The method of claim 9 wherein said halogenated xanthene is Rose Bengal.

11. The method of claim 9 wherein said halogenated xanthene includes as a functional derivative a targeting moiety selected from the group comprising deoxyribonucleic acid (DNA), ribonucleic acid (RNA), amino acids, proteins, antibodies, ligands, haptens, carbohydrate receptors or complexing agents, lipid receptors or complexing agents, protein receptors or complexing agents, chelators, and encapsulating vehicles.

12. The method of claim 9 herein said imaging is accomplished through a method selected from the group comprising computerized axial tomography (CAT), fluorography and magnetic resonance imaging (MRI).

13. A method of imaging diseased tissue comprising the steps of:
   administering to a patient an x-ray or magnetic resonance imaging (MRI) contrast agent prior to imaging, a portion of said contrast agent being retained in said diseased tissue; and thereafter
   imaging said patient with x-rays or MRI to identify said diseased tissue;
   wherein said contrast agent comprises a halogenated xanthene.

14. The method of claim 13 wherein said halogenated xanthene is Rose Bengal.

15. The method of claim 13 wherein said halogenated xanthene includes as a functional derivative a targeting moiety selected from the group consisting of deoxyribonucleic acid (DNA), ribonucleic acid (RNA), amino acids, proteins, antibodies, ligands, haptens, carbohydrate receptors or complexing agents, lipid receptors or complexing agents, protein receptors or complexing agents, chelators, and encapsulating vehicles.

16. The method of claim 13 wherein said imaging is accomplished through a method selected from the group consisting of computerized axial tomography, fluorography and magnetic resonance imaging.

17. The method of claim 13 wherein said halogenated xanthene is selected from the group consisting of iodinated and brominated halogenated xanthenes.

18. The method of claim 13 wherein said halogenated xanthene is selected from the group consisting of Rose Bengal, Phloxine B, Erythrosin B and Eosin Y.

19. The method of claim 13 wherein said imaging contrast agent is detected based on magnetic resonance of aromatic protons in said halogenated xanthene.

20. The method of claim 13 wherein of said imaging contrast agent is detected based on magnetic resonance of aromatic halides in said halogenated xanthene.

21. A method of imaging tissue comprising the steps of:
   administering to a patient an x-ray or magnetic resonance imaging (MRI) contrast agent prior to imaging, a portion of said contrast agent being retained in said tissue; and thereafter
   imaging said patient with x-rays or MRI to identify said tissue;
   wherein said contrast agent comprises a halogenated xanthene.

22. The method of claim 21 wherein said halogenated xanthene is Rose Bengal.

* * * * *